(12) United States Patent
Koike et al.

(10) Patent No.: US 6,852,758 B2
(45) Date of Patent: Feb. 8, 2005

(54) OIL COMPOSITION

(75) Inventors: Shin Koike, Tokyo (JP); Naoki Hosoya, Tokyo (JP); Takeshi Yasumasu, Tokyo (JP)

(73) Assignee: Kao Corporation, Tokyo (JP)

( * ) Notice: Subject to any disclaimer, the term of this patent is extended or adjusted under 35 U.S.C. 154(b) by 118 days.

(21) Appl. No.: 10/061,286

(22) Filed: Feb. 4, 2002

(65) Prior Publication Data

US 2003/0072858 A1 Apr. 17, 2003

Related U.S. Application Data

(63) Continuation of application No. PCT/JP00/04499, filed on Jul. 6, 2000.

(30) Foreign Application Priority Data

Aug. 3, 1999 (JP) ............................................ 11-220012
Aug. 26, 1999 (JP) ............................................ 11-239970

(51) Int. Cl.$^7$ ........................ A61K 31/20; A61K 31/22; A61K 31/225
(52) U.S. Cl. ........................ 514/560; 514/546; 514/547; 514/558
(58) Field of Search .............................. 514/562, 558, 514/546, 547

(56) References Cited

U.S. PATENT DOCUMENTS

| | | |
|---|---|---|
| 4,976,984 A | 12/1990 | Yasukawa et al. |
| 6,004,611 A | 12/1999 | Gotoh et al. |
| 6,337,414 B1 | 1/2002 | Sugiura et al. |
| 6,361,980 B2 | 3/2002 | Sugiura et al. |

FOREIGN PATENT DOCUMENTS

| | | |
|---|---|---|
| FR | 2 599 382 | 12/1987 |
| JP | 62-132808 | 6/1987 |
| JP | 63-104917 A | 5/1988 |
| JP | 64-002589 | 1/1989 |
| JP | 1-160988 | 6/1989 |
| JP | 1-174342 | 7/1989 |
| JP | 2-011516 | 1/1990 |
| JP | 2-045424 | 2/1990 |
| JP | 02-190146 | 7/1990 |
| JP | 4-300825 | 10/1992 |
| JP | 4-300826 | 10/1992 |
| JP | 4-300828 | 10/1992 |
| JP | 08-060181 | 3/1996 |
| JP | 8-214892 | 8/1996 |
| JP | 10-057086 | 3/1998 |
| JP | 10-176181 A | 6/1998 |
| JP | 10-265795 | 10/1998 |
| WO | WO 96/37586 | 11/1996 |
| WO | WO 01/01787 | 1/2001 |
| WO | WO 01/15542 | 3/2001 |
| WO | WO 02/11551 | 2/2002 |

OTHER PUBLICATIONS

Z. Li, et al., Biotechnology Letters, vol. 15, No. 4, pp. 393–398, XP–000105786, "Stability of Microbial Lipase in Alcoholysis of Fish Oil During Repeated Enzyme Use", Apr. 1993.

Front Page of International Application No. PCT/JP00/04499 (2–sided, copied single sided) 2 pp.

Y. Tanaka, et al., Jaocs, vol. 69 No. 12, pp. 1210–1214, "Concentration of Docosahexaenoic Acid in Glyceride by Hydrolysis of Fish Oil with *Candida Cylindracea Lipase*", Dec. 1992.

T. Hoshino, et al., Agric. Biol. Chem., vol. 54, No. 6, pp. 1459–1467, "Selective Hydrolysis of Fish Oil by Lipase to Concentrate n–3 Polyunsaturated Fatty Acids", 1990.

Zu–Yi et al., Jaocs, vol. 70, No. 8, pp. 745–748, "Lipase–Catalyzed Esterification of Glycerol and n–3 Polyunsaturated Fatty Acid Concentrate in Organic Solvent", Aug. 1993.

B. Myrnes, et al., Jaocs, vol. 72, No. 11, pp. 1339–1344, "Solvent–free Enzymatic Glycerolysis of Marine Oils", 1995.

Y. Shimada, et al., Jaocs, vol. 72, No, 12, pp. 1577–1581, "Selective Hydrolysis of Polyunsaturated Fatty Acid–Containing Oil with *Geotrichum Candidum Lipase*", 1995.

H. Breivik, et al., Jaocs, vol. 74, No. 11, pp. 1425–1429, "Preparation of Highly Purified Concentrates of Eicosapentaenoic Acid and Docosahexaenoic Acid", 1997.

*Primary Examiner*—Kevin E. Weddington
(74) *Attorney, Agent, or Firm*—Oblon, Spivak, McClelland, Maier & Neustadt, P.C.

(57) ABSTRACT

The invention relates to oil composition comprising 0.1 to 59.8% by weight of a triglyceride, 40 to 99.7% by weight of a diglyceride, 0.1 to 10% by weight of a monoglyceride and at most 5% by weight of a free fatty acid, wherein contents of ω3 type unsaturated acyl groups having at least 20 carbon atoms and monoenoic acyl groups in acyl groups constituting the diglyceride are 15 to 89.5% by weight and 10 to 84.5% by weight, respectively; and oral medicinal compositions and foods comprising such an oil composition.

The oil composition effectively develops physiological functions derived from ω3 type unsaturated fatty acids, such as inhibition of platelet aggregation, and is excellent in effect of facilitating combustion of body fat, oxidation stability, flavor and the like, and also excellent in flowability.

14 Claims, No Drawings

OIL COMPOSITION

This application is a CON of PCT/JP00/04499 filed Jul. 6, 2000.

BACKGROUND OF THE INVENTION

1. Field of the Invention

The present invention relates to an oil or fat (hereafter referred to as "oil" merely) composition which effectively develops physiological functions derived from ω3 type unsaturated fatty acids having at least 20 carbon atoms, such as inhibition of platelet aggregation, and is excellent in effect of facilitating combustion of body fat, oxidation stability, flowability, flavor and the like, and oral medicinal compositions and foods comprising such an oil composition.

2. Discussion of the Background

In recent years, it has been clarified that diglycerides can have an obesity-preventing effect, an effect to prevent an increase in weight, etc. (Japanese Patent Application Laid-Open No. 300828/1992, etc.), and it is attempted to incorporate these into various kinds of foods. It has been reported that when a glyceride mixture containing diglycerides at a high concentration is used in an oil phase, an edible oil-in-water type emulsion composition have a rich fatty feel and is good in flavor even when a fat content is decreased (Japanese Patent No. 2848849).

On the other hand, it has been known that ω3 type unsaturated fatty acids having at least 20 carbon atoms, such as docosahexaenoic acid (DHA) and eicosapentaenoic acid (EPA) are mainly contained in the form of triglyceride in fish oil and the like in abundance and can have effective physiological activities such as anti-platelet aggregation property, antitumor activity, immune activation, antiallergic activity, improvement in brain function and improvement in visual function.

As oils highly containing such diglycerides and ω3 type unsaturated fatty acids, there have been known, for example, a natural oil that DHA among constitutive fatty acids of the oil is contained in a proportion of at least 60%, and the total content of diglycerides and monoglycerides is at least 80% of the oil (Japanese Patent Application Laid-Open No. 60181/1996), and the like.

However, the ω3 type unsaturated fatty acids having at least 20 carbon atoms are very poor in oxidation stability. When an ω3 type unsaturated fatty acid is oxidized, the oxidized unsaturated fatty acid involves a problem that not only its physiological activity functions are lost, but also the living body is adversely affected when such an unsaturated fatty acid is taken. In addition, an oil highly containing such an ω3 type unsaturated fatty acid has an unpleasant flavor derived from its raw oil, and so a problem is offered when it is used in food in particular. Further, ω3 type unsaturated fatty acids involve a problem that when they are converted into their corresponding diglycerides, the viscosity of the resulting diglycerides becomes high, so that the physiological activities of the ω3 type unsaturated fatty acids are hard to be developed.

It is therefore an object of the present invention to provide an oil composition which is good in flowability, resistance to oxidation and excellent in flavor, effectively develops physiological activities of an ω3 type unsaturated fatty acids having at least 20 carbon atoms, and is excellent in effect of facilitating combustion of body fat, and oral medicinal compositions and foods comprising such an oil composition.

SUMMARY OF THE INVENTION

The present inventors have attracted attention to the compositions of acyl groups constituting a diglyceride and found that when an ω3 type unsaturated acyl group having at least 20 carbon atom and a monoenoic acyl group as acyl groups constituting a diglyceride are contained in specified amounts in an oil composition comprising a triglycerides, diglyceride, monoglyceride and free fatty acid in specified proportions, an oil composition which is hard to be oxidized, good in flowability and excellent in flavor, effectively develops physiological activities of an ω3 type unsaturated fatty acids, and is excellent in effect of facilitating combustion of body fat is provided.

The present invention provides an oil composition comprising 0.1 to 59.8% by weight (hereafter indicated merely by "%") of a triglyceride, 40 to 99.7% of a diglyceride, 0.1 to 10% of a monoglyceride and at most 5% of a free fatty acid, wherein contents of an ω3 type unsaturated acyl groups having at least 20 carbon atoms and monoenoic acyl groups in acyl groups constituting the diglyceride are 15 to 89.5% and 10 to 84.5%, respectively.

The present invention also provides an oral medicinal composition comprising such an oil composition.

The present invention further provides a food comprising such an oil composition.

DETAILED DESCRIPTION OF THE PREFERRED EMBODIMENTS

In the present invention, no particular limitation is imposed on the number of carbon atoms in acyl groups constituting the triglyceride. However, the number of carbon atoms is preferably 8 to 24, particularly 16 to 22. The content of unsaturated acyl groups is preferably at least 55%, more preferably at least 70%, particularly preferably at least 90% based on all the acyl groups in the triglyceride. The triglyceride can be obtained from a vegetable oil such as soybean oil, rapeseed oil, palm oil, rice oil or corn oil, an animal oil such as beef tallow or fish oil, or a hardened oil, fractionated oil or random transesterified oil thereof. The content of the triglyceride in the oil composition according to the present invention must be 0.1 to 59.8%, preferably 5 to 55%. When the content of the triglyceride is 0.1 to 59.8%, and the content of the monoglyceride is 0.1 to 10%, unpleasant flavor derived from the free fatty acid and raw fib oil can be masked to improve the flavor of the resulting oil composition and also the oxidation stability thereof.

In the present invention, the acyl groups constituting the diglyceride include ω3 unsaturated acyl groups having at least 20 carbon atoms in a proportion of 15 to 89.5%, preferably 20 to 70%, particularly preferably 25 to 65%, most preferably 50 to 65% based on all the acyl groups in the diglyceride and monoenoic acyl groups in a proportion of 10 to 84.5%, preferably 12 to 45%, particularly preferably 12 to 35%, most preferably 14 to 25%. The term "ω3 type unsaturated acyl group" as used herein means an acyl group that a first unsaturated bond is located on the third carbon atom from an ω position when the positions of unsaturated bonds are specified from the ω position, and that has at least 2 unsaturated bonds. As the ω3 type unsaturated acyl groups having at least 20 carbon atoms, are preferred eicosapentaenoyl and docosahexaenoyl groups. The monoenoic acyl group is an acyl group having a carbon-carbon double bond. As examples thereof, are preferred hexadecamonoenoyl, octadecamonoenoyl, eicosamonoenoyl and docosamonoenoyl groups.

In the present invention, the acyl groups constituting the diglyceride preferably include ω6 type unsaturated acyl groups. The term "ω6 type unsaturated acyl group" as used herein means an acyl group that a first unsaturated bond is located on the sixth carbon atom from an ω position when the positions of unsaturated bonds are specified from the ω position, and that has at least 2 unsaturated bonds. When the ω6 type unsaturated acyl groups are contained, development of drug intoxication such as hemolysis and hemorrhage, which are caused by excess ingestion of the ω3 type unsaturated acyl groups, can be inhibited and development of the physiological activities of the ω6 type unsaturated acyl groups can be facilitated. Examples of the ω6 type unsaturated acyl groups include a linoleyl group (cis,cis-9, 12-octadecadienoyl group), a γ-linolenyl group (all cis-6,9, 12-octadecatrienoyl group) and an arachidonyl group (all cis-5,8,11,14-eicosatetraenoyl group), with the linoleyl group being preferred. The content of the ω6 type unsaturated acyl groups in all the acyl groups in the diglyceride is preferably 0.5 to 75%, more preferably 0.5 to 50%, particularly preferably 1 to 25%, most preferably 1 to 15% in order to more remarkably develop the above-described effects of the present invention.

The diglyceride can be obtained by an optional process such as transesterification of any of various oils such as fish oil and rapeseed oil containing ω3 type unsaturated acyl groups, monoenoic acyl groups, ω6 type unsaturated acyl groups, etc. with glycerol or esterification of a fatty acid derived from such an oil with glycerol. Among these processes, the former process is particularly preferred. The reaction method thereof may be either a chemical reaction method making use of an alkali catalyst such as sodium methoxide, or the like or a biochemical reaction method making use of a lipolytic enzyme such as lipase. The content of such a diglyceride in the oil composition according to the present invention must be 40 to 99.7%, preferably 50 to 95%, particularly preferably 60 to 90%. When the content is 40 to 99.7%, the development of the physiological activities derived from the ω3 type unsaturated fatty acids is facilitated, and the effect of facilitating combustion of body fat becomes excellent.

In the present invention, a glyceride polymer may preferably be contained in order to improve the oxidation stability. The glyceride polymer is a polymer obtained by intermolecular polymerization of a glyceride such as a triglyceride, diglyceride or monoglyceride (for example, "Kagaku to Seibutu (Chemistry and Organism), Vol. 21, page 179, 1983), and no particular limitation is imposed on the polymerization degree of the glyceride, the positions of fatty acid esters, the kinds of acyl groups constituting the fatty acid esters, etc. The content of the glyceride polymer in the oil composition is preferably 0.1 to 10%, more preferably 0.1 to 5%, particularly preferably 0.2 to 2% from the viewpoints of improvement in oxidation stability of the oil composition and flavor. The amount of such a glyceride polymer can be controlled by suitably controlling reaction temperature conditions and the like upon synthesis of the glyceride polymer. The glyceride polymer can be determined by an HPLC process in which a gel permeation chromatographic column is connected.

The content of the monoglyceride in the oil composition according to the present invention must be 0.1 to 10%, preferably 0.1 to 5% from the viewpoint of improvement in the flavor of the oil composition. The content of free fatty acids must be at most 5%, preferably at most 2% from the viewpoint of improvement in the flavor of the oil composition.

The oil composition according to the present invention can be prepared by mixing the above-described components and suitably subjecting the resulting mixture to heating, stirring and/or the like. Alternatively, the oil composition according to the present invention can be obtained by fractionating triglycerides, diglycerides, monoglycerides, glyceride polymers, free fatty acids and the like obtained by transesterification of an oil containing ω3 type unsaturated acyl groups, ω6 type unsaturated acyl groups, monoenoic acyl groups and the like, such as fish oil or rapeseed oil, with glycerol, and then suitably mixing these fractionation products with one another. The oil composition according to the present invention can also be obtained by subjecting the reaction product obtained according to the above-described preparation process of the diglyceride to ordinary purification treatments such as molecular distillation, deodorizing and decolorizing.

The oil composition thus obtained has excellent physiological activities such as effects of facilitating combustion of body fat, reducing blood sugar value, consuming triglyceride in blood, reducing insulin in blood, improving liver function, reducing blood pressure, and inhibiting activation of plasminogen in addition to inhibitory effect on platelet aggregation, is good in digestibility because it is excellent in flowability, can be stored over a long period of time because it is excellent in oxidation stability, and moreover is excellent in flavor. In particular, since the ω3 type unsaturated acyl groups having at least 20 carbon atoms are present as acyl groups constituting the diglyceride, the oil composition acts at a lower concentration than the case where they are present as free fatty acids, and so it has good fast-acting property, and is good in flavor and safe. Since the oil composition according to the present invention has such excellent properties, it can be utilized for oral medicinal compositions and foods.

No particular limitation is imposed on the forms of the oral medicinal compositions, and examples thereof include solid preparations such as powder preparations, granule preparations, capsule preparations, pill preparations and tablet preparations; and liquid preparations such as aqueous preparations, suspension preparations and emulsion preparations. Such an oral preparation can be prepared by adding an excipient, a disintegrant, a binder, a lubricant, a surfactant, an alcohol, water, a water-soluble polymer, an sweet flavor, a taste corrigent, an acid flavor and/or the like commonly used according to the form of the oral preparation in addition to the oil composition in accordance with a method known per se in the art. Examples of oral medicinal compositions include platelet aggregation inhibitors, body weight-reducing agents, brain function improvers, visual function improvers and diabetes improvers. It is preferred that the amount of the oil composition according to the present invention to be incorporated in the oral medicinal composition be generally 0.1 to 100%, particularly 1 to 80% though it varies according to the application and form of the oral medicinal composition. The oral medicinal composition is preferably administered in a dose of 0.1 to 50 g per day in terms of the oil composition. Meanwhile, the administration may be once per day, or may be divided into several times per day.

With respect to the foods, the oil composition may be used as oil-containing foods containing the oil composition as a part of food. Examples of such oil-containing foods include healthy foods that the specified functions are exhibited to promote health. Specific examples thereof include tablet preparations, granule preparations, dressings such as French dressing, mayonnaises, creams, bakery foods such as bread and cookie, confectionery such as chocolates and potato chips, and drinks, in which such an oil composition is incorporated. Such oil-containing food can be produced by adding food materials commonly used according to the kind of the oil-containing food in addition to the oil composition in accordance with a method known per se in the art. It is preferred that the amount of the oil composition according to the present invention to be incorporated in food be generally 0.1 to 100%, particularly 1 to 80% though it varies according to the kind of the food. It may also be used as a food material of oils for deep fried foods such as tempura and fries, or oils for pan fried foods.

Having generally described this invention, a further understanding can be obtained by reference to certain specific examples which are provided herein for purposes of illustration only and are not intended to be limiting unless otherwise specified.

EXAMPLES

Example 1

Fish oil (product of Kao Corporation; 200 parts by weight) and glycerol (product of Wako Pure Chemical Industries, Ltd.; 8 parts by weight) were mixed with each other, and an alkali catalyst (sodium methoxide, $CH_3ONa$; 0.6 parts by weight) was mixed to the resultant mixture to conduct transesterification at 100° C. for 4 hours under reduced pressure (0.133 kPa). The reaction product thus obtained was fractionated by column chromatography on silica gel, and a triglyceride (56.1 parts by weight), a diglyceride (42.9 parts by weight) and a monoglyceride (1.0 part by weight) among the resultant fractionation products were mixed with one another to prepare Oil Composition 1.

Example 2

A triglyceride (56.0 parts by weight), a diglyceride (42.7 parts by weight), a monoglyceride (1.1 parts by weight) and a glyceride polymer (0.2 parts by weight) among the respective fractionation products obtained in Example 1 were mixed with one another to prepare Oil Composition 2.

Example 3

A high DHA-containing oil ("DHA-45", product of MARUHA CORP.; 200 parts by weight) and glycerol (10 parts by weight) were mixed with each other to conduct transesterification and fractionation of respective components in a similar manner to Example 1. A triglyceride (10.3 parts by weight), a diglyceride (87.4 parts by weight), a monoglyceride (1.9 parts by weight) and a glyceride polymer (0.4 parts by weight) were then mixed with one another to prepare Oil Composition 3.

Comparative Examples 1 and 2

Rapeseed oil (product of Nisshin Oil Mills, Ltd.) and fish oil were provided as Oil Composition 4 (Comparative Example 1) and Oil Composition 5 (Comparative Example 2).

Comparative Example 3

Rapeseed oil (200 parts by weight) and glycerol (10 parts by weight) were mixed with each other to conduct transesterification and fractionation of respective components in a similar manner to Example 1. A triglyceride (21.7 parts by weight), a diglyceride (76.5 parts by weight), a monoglyceride (1.3 parts by weight) and a free fatty acid (0.5 parts by weight) were then mixed with one another to prepare Oil Composition 6.

Comparative Example 4

A high DHA-containing oil (100 parts by weight), hydrogenated coconut oil (product of Kao Corporation; 100 parts by weight) and glycerol (8 parts by weight) were mixed with each other to conduct transesterification and fractionation of respective components in a similar manner to Example 1. A triglyceride (41.6 parts by weight) and a diglyceride (58.4 parts by weight) were then mixed with each other to prepare Oil Composition 7.

Comparative Example 5

A triglyceride (56.7 parts by weight) and a diglyceride (43.7 parts by weight) among the respective fractionation products obtained in Example 1 were mixed with each other to prepare Oil Composition 8.

Example 4

A high DHA-containing oil ("DHA-45", product of MARUHA CORP.; 100 parts by weight) and glycerol (40 parts by weight) were mixed with each other, and sodium methoxide (0.3 parts by weight) was mixed to the resultant mixture to conduct transesterification at 100° C. for 4.5 hours under reduced pressure (0.266 to 0.399 kPa). The resultant reaction product was subjected to molecular distillation, treatment with citric acid and then decolorizing treatment with activated carbon, further washed with water and deodorized (subjected to steaming). The purified product (Oil Composition 9) thus obtained had a composition: triglyceride 44.9% by weight; diglyceride 54.2% by weight; monoglyceride 0.6% by weight; free fatty acid 0.1% by weight; and glyceride polymer 0.2% by weight.

Principal fatty acid compositions of diglyceride fractions derived from the respective oils obtained in Examples 1, 3 and 4 and Comparative Examples 3 and 4 are shown in Table 1.

TABLE 1

|  |  | Example | | | Comp. Example | |
| --- | --- | --- | --- | --- | --- | --- |
|  |  | 1 | 3 | 4 | 3 | 4 |
| ω3 | C18:3 | 0 | 0 | 0 | 10.3 | 0 |
|  | C20:5 | 15.2 | 6.7 | 6.7 | 0 | 3.8 |
|  | C22:6 | 8.4 | 46.3 | 46.3 | 0 | 24.1 |
| Monoenoic | C16:1 | 9.1 | 3.4 | 3.4 | 0 | 1.5 |
|  | C18:1 | 4.3 | 10.5 | 10.5 | 49.8 | 4.8 |
|  | C20:1 | 5.5 | 1.4 | 1.4 | 0 | 0.5 |
|  | C22:1 | 5.2 | 1.1 | 1.1 | 0 | 0.3 |
| ω6 | C18:2 | 2.0 | 1.3 | 1.3 | 29.1 | 0.6 |
|  | C18:3 | 1.3 | 0.7 | 0.7 | 0 | 0.3 |
| Saturated | C16:0 | 0 | 0 | 0 | 0 | 22.8 |
|  | C14:0 | 5.8 | 2.2 | 2.2 | 0 | 9.6 |
|  | C16:0 | 16.9 | 11.3 | 11.3 | 8.1 | 10.2 |
|  | C18:0 | 3.5 | 2.7 | 2.7 | 2.7 | 7.4 |

Measured by gas chromatography after methylation.

Test Example 1

Investigation of inhibitory effect on platelet aggregation:

Wistar male rats aged 10 weeks were divided into 9 groups, and a feed containing rapeseed oil (10%) and one (3%) of Oil Compositions 1 to 9 was given to its corresponding group for 2 weeks. Blood was then collected from each rat to determine the inhibitory effect of each test composition on platelet aggregation in accordance with the method described in J. Nutri., Vol. 124, page 1898 (1994). The results are shown in Table 2. In the table, the numerical values indicate relative values that a value in the case where Oil Composition 4 was used was regarded as 100. The smaller relative value indicates that platelet is harder to aggregate.

TABLE 2

| Oil Composition | Relative value |
| --- | --- |
| 1 | 81 |
| 2 | 81 |
| 3 | 64 |
| 4 | 100 |
| 5 | 95 |
| 6 | 106 |

TABLE 2-continued

| Oil Composition | Relative value |
|---|---|
| 7 | 93 |
| 9 | 69 |

Oil Compositions 1 to 3 exhibited a platelet aggregation-inhibiting effect superior to Oil Compositions 4 to 7. Particularly excellent effect was achieved in the case where among these compositions, Oil Compositions 3 and 9, in which the content of the ω3 type unsaturated acyl groups in all the acyl groups in the diglyceride was at least 50%, were each used.

Test Example 2

Wistar male rats aged 10 weeks were divided into 3 groups each containing 8 rats, and a feed having a composition shown in Table 3 was given to each group for 2 weeks. After the rats were starved for 18 hours, blood was collected through an abdominal aorta of each rat under ether anesthesia to conduct a biochemical test of the blood. At the same time, liver and perirenal adipose tissues were taken out of the rat to measure their weight. Thereafter, a portion (0.5 g) thereof was homogenized by means of a glass homogenizer in a mixed solvent (10 mL) of chloroform and methanol (1:1) and filtered with suction through glass fiber filter paper (GA100, 47 mm).

Physiological saline was added to the filtrate and the mixture was moderately stirred and then centrifuged (3000 rpm) for 10 minutes to conduct phase separation. A lower layer was taken out and dried to solid under a nitrogen stream. The resultant solid was dissolved again in a proper amount of n-hexane and the solution was dried over anhydrous sodium sulfate. The solvent was removed and the residue was dried to solid under a nitrogen stream again. The resultant solid was dissolved in 2-propanol (5 mL) to provide a test solution for lipid quantitative analysis.

A body fat ratio was measured by a body fat meter (EM-SCAN SA-2, product of Central Kagaku Boueki) for small animal.

Triglyceride contents in the blood, liver, and perirenal adipose tissues were determined by a Triglyceride Test Wako (manufactured by Wako Pure Chemical Industries, Ltd.). A total cholesterol quantity in the liver was determined by a Cholesterol E Test Wako (manufactured by Wako Pure Chemical Industries, Ltd.). GOT (glutamic oxaloacetic transaminase) activity and GPT (glutamic pyruvic transaminase) activity in the blood were determined by separating sera and then using aspartic acid and alanine as substrates, respectively, in accordance with the Karmen method (J. Clin. Invest., Vol. 34, page 131 (1955)). The results are shown in Table 4.

TABLE 3

|  | Control | Test group (%) |
|---|---|---|
| Casein | 20 | 20 |
| Corn oil | 10 | 10 |
| Oil | 0 | 3*[1] |
| Mineral mixture | 4 | 4 |
| Vitamin mixture | 1 | 1 |
| Cellulose | 4 | 4 |
| Choline chloride | 0.15 | 0.15 |
| Starch | 60.85 | 57.85 |

*[1]The kind of the oil are shown in Table 4.

TABLE 4

| Result (relative value) Control = 100 | Body fat ratio | TG content in liver | TG content in peri-renal adipose tissues | TG content in blood | GOT | GPT | Total cholesterol content in liver |
|---|---|---|---|---|---|---|---|
| Corn oil 10%, Comp. Ex. (Control) | 100 | 100 | 100 | 100 | 100 | 100 | 100 |
| Corn oil + Oil Comp'n 6 Comp. Ex. | 101 | 118 | 104 | 115 | 127 | 116 | 105 |
| Corn oil + Oil Comp'n 9 Example | 80 | 37 | 86 | 71 | 63 | 59 | 87 |

It is understood from the results shown in Table 4 that in the group that the feed obtained by adding the oil composition (3%) according to the present invention to corn oil (10%) was ingested, excellent body fat-reducing effect is achieved, and the triglyceride content in perirenal adipose tissues, the triglyceride content in the liver, the total cholesterol content in the liver, the serum transaminase levels (GOT, GPT) and the triglyceride content in the blood can also be reduced.

Test Example 3

Oil Composition 9 charged into a soft capsule was ingested by 3 healthy men (A, B and C) for 6 weeks in a dose of 1 g per day without changing their eating habits to measure their BMI [Body Mass Index: (weight kg)/(height m×height m)], body fat ratio and waist sizes. The results are shown in Table 5.

TABLE 5

|  |  | After 0 week | After 6 weeks |
|---|---|---|---|
| A: aged 39 years | BMI | 25.0 | 24.7 |
|  | Body fat ratio (%) | 25.1 | 24.2 |
|  | Waist (cm) | 88.2 | 87.0 |
| B: aged 36 years | BMI | 23.8 | 23.3 |
|  | Body fat ratio (%) | 24.0 | 23.5 |
|  | Waist (cm) | 85.7 | 84.9 |
| C: aged 32 years | BMI | 24.1 | 23.4 |
|  | Body fat ratio (%) | 24.7 | 24.1 |
|  | Waist (cm) | 87.6 | 86.1 |

It is understood from the results shown in Table 5 that when the oil composition according to the present invention is ingested, the body fat ratio can be reduced without changing the eating habit, and correspondingly BMI and waist size can be reduced.

Test Example 4

Ten healthy men having BMI of at least 24 (body fat ratio of at least 23%; light obesity) were procured to orally ingest Oil Composition 9 molded in the form of a capsule in a dose of 2 g per day to determine their insulin concentrations in blood before beginning of the ingestion and after completion of the ingestion. As a result, the average value of the insulin concentrations in blood was 16.3 $\mu$U/mL before beginning of the ingestion (initial value), while the value was markedly reduced to 12.9 $\mu$U/mL after completion of the ingestion (1 month) ($p<0.05$). From this result, it was confirmed that the oil composition according to the present invention can significantly reduce the insulin concentration in blood.

Test Example 5

Oil Composition 9 charged into a soft capsule was ingested by 3 men (A, B and C) having a fasting blood sugar level of 120 mg/dl or more for 3 months in a dose of 2 g per day without changing their eating habits. Thereafter, their blood sugar levels were measured by a Glucose Test Wako (manufactured by Wako Pure Chemical Industries, Ltd.). The results are given in Table 6. From the results, it was indicated that the blood sugar levels of all the men were reduced. It was confirmed by this result that the blood sugar reducing agents according to the present invention are useful in reducing a blood sugar level and further in preventing and improving diabetes.

TABLE 6

|  | Initial value | After 3 months |
|---|---|---|
| A: aged 39 years | 123 | 101 |
| B: aged 45 years | 135 | 110 |
| C: aged 42 years | 142 | 103 |
|  | (mg/dl) |  |

Test Example 6

Investigation of oxidation stability of oil composition:

With respect to Oil Compositions 1 to 3, 5, 8 and 9, the induction time was determined in accordance with the following method (CDM test version: standard oils and fats analyzing test method (edited by The Japan Oil Chemists' Society). More specifically, while a sample was heated to 90° C. in a reaction vessel, clean air was introduced to collect volatile decomposition products formed by oxidation in water, thereby measuring the time (hr) up to a turning point where the electric conductivity of water rapidly changed. The results are shown in Table 7. In the table, the numerical values indicate relative values that the time up to the turning point of Oil Composition 5 was regarded as 100. The greater relative value indicates that the oxidation stability is better.

TABLE 7

| Oil Composition | Relative value |
|---|---|
| 1 | 103 |
| 2 | 125 |
| 3 | 128 |
| 5 | 100 |
| 8 | 94 |
| 9 | 133 |

Oil Compositions 1 to 3 and 9 were superior in oxidation stability to Oil Compositions 5 and 8.

Test Example 8

Investigation of flowability of oil composition:

With respect to Oil Compositions 1 to 3, 7 and 9, the viscosity was measured by means of an oscillational viscometer (40° C., 50 Hz). The results are shown in Table 8.

TABLE 8

| Oil Composition | Viscosity (mPa · s) |
|---|---|
| 1 | 61 |
| 2 | 62 |
| 3 | 45 |
| 7 | 105 |
| 9 | 40 |

Oil Compositions 1 to 3 and 9 had a viscosity not higher than 100 mPa·s, and it was confirmed that the viscosity of an oil can be reduced to 100 cp or lower by containing monoenoic acyl groups in a proportion of at least 10% based on all the acyl groups in the diglyceride. The viscosity is reduced to 100 mPa·s, preferably 70 mPa·s, whereby micelle of bile acid is easily formed upon ingestion of the resulting oil composition, and so the digestion of the oil composition is improved, and the development of the physiological activities is facilitated.

Test Example 9

Evaluation of French dressing containing Oil Composition 3, 4, 8 or 9 as to flavor:

An oil composition-containing French dressing was prepared in accordance with its corresponding formulation shown in Table 9 to evaluate it as to flavor. More specifically, wine vinegar was mixed with common salt, pepper and mustard. Its corresponding Oil Composition and salad oil were added to the resultant mixture while stirring by a whipper. The resultant mixture was sufficiently stirred to prepare a French dressing. The dressing was put on coleslaw to evaluate it as to flavor by ten panelists in accordance with the following evaluation standard. The average values of evaluation scores are shown in Table 9.

Evaluation standard:

4: Very delicious;
3: Somewhat delicious;
2: Not very delicious;
1: Not delicious;

TABLE 9

| Test No. | 1 | 2 | 3 | 4 |
|---|---|---|---|---|
| Salad oil | 30.0 | 30.0 | 30.0 | 30.0 |
| Wine vinegar | 50.0 | 50.0 | 50.0 | 50.0 |
| Common salt | 2.5 | 2.5 | 2.5 | 2.5 |
| Pepper | 0.6 | 0.6 | 0.6 | 0.6 |
| Mustard | 0.5 | 0.5 | 0.5 | 0.5 |
| Oil Composition 3 | 60.0 | — | — | — |
| Oil Composition 4 | — | 60.0 | — | — |
| Oil Composition 8 | — | — | 60.0 | — |
| Oil Composition 9 | — | — | — | 60.0 |
| Average value of flavor | 3.2 | 3.5 | 1.7 | 3.2 |

(Unit of amounts incorporated: parts by weight)

The French dressings using Oil Compositions 3 and 9, respectively, had substantially the same excellent flavor as that using Oil Composition 4. Belching after ingestion had no unpleasant feel. On the other hand, the French dressing using Oil Compositions 8 was poor in flavor, and belching after ingestion had an unpleasant feel.

Test Example 10

Evaluation of oral syrup preparation containing Oil Composition 1, 2, 3, 4, 8 or 9 as to flavor:

An oral syrup preparation was prepared in accordance with its corresponding formulation shown in Table 10. More specifically, after sodium benzoate and purified sucrose were added to a proper amount of heated purified water into a solution, hydroxypropyl cellulose was added, and the mixture was stirred by a homomixer into a solution, thereby preparing Liquid A. On the other hand, sucrose fatty acid ester was dispersed in its corresponding Oil Composition to prepare Liquid B. Liquid B was added while stirring Liquid A by the homomixer, and purified water was added thereto, thereby formulating an oral syrup preparation. The syrup preparations thus obtained were evaluated as to flavor in the same manner described in Test Example 9. The results are shown in Table 10.

As described above, the oil compositions according to the present invention are hard to be oxidized because the content of the $\omega 3$ type unsaturated acyl group-containing diglyceride is relatively low, is excellent in flavor and can effectively exhibit the physiological activities of $\omega 3$ type unsaturated fatty acids.

TABLE 10

| Test No. | 5 | 6 | 7 | 8 | 9 | 10 |
|---|---|---|---|---|---|---|
| Hydroxypropyl cellulose | 0.5 | 0.5 | 0.5 | 0.5 | 0.5 | 0.5 |
| Purified sucrose | 50.0 | 50.0 | 50.0 | 50.0 | 50.0 | 50.0 |
| Sucrose fatty acid ester | 0.2 | 0.2 | 0.2 | 0.2 | 0.2 | 0.2 |
| Na benzoate | 0.06 | 0.06 | 0.06 | 0.06 | 0.06 | 0.06 |
| Oil Composition 1 | 5.0 | — | — | — | — | — |
| Oil Composition 2 | — | 5.0 | — | — | — | — |
| Oil Composition 3 | — | — | 5.0 | — | — | — |
| Oil Composition 4 | — | — | — | 5.0 | — | — |
| Oil Composition 8 | — | — | — | — | 5.0 | — |
| Oil Composition 9 | — | — | — | — | — | 5.0 |
| Purified water | 44.24 | 44.24 | 44.24 | 44.24 | 44.24 | 44.24 |
| Average value of flavor | 3.1 | 3.1 | 3.4 | 3.7 | 2.2 | 3.5 |

(Unit of amounts incorporated: parts by weight)

The oral syrup preparations using Oil Compositions 1, 2, 3 and 9, respectively, had substantially the same excellent flavor as that using Oil Composition 4. Belching after ingestion had no unpleasant feel. On the other hand, the oral syrup preparation using Oil Compositions 8 was poor in flavor, and belching after ingestion had an unpleasant feel.

Industrial Applicability

The oil compositions according to the present invention are hard to be oxidized, good in flowability and excellent in flavor, can effectively develop physiological activities of $\omega 3$ type unsaturated fatty acids having at least 20 carbon atoms, and are excellent in effect of facilitating combustion of body fat.

Obviously, numerous modifications and variations of the present invention are possible in light of the above teachings. It is therefore to be understood that within the scope of the appended claims, the invention may be practiced otherwise than as specifically described herein.

This application is based in part on Japanese patent application JP 11/220012 filed with the Japanese patent office on Aug. 3, 1999 and international application WO/01/1/989, filed with the Japanese receiving office of WIPO on Jul. 6, 2000, the entire contents of each being hereby incorporated by reference.

What is claimed as new and desired to be secured by Letters Patent of the United States is:

1. A method of preparing an oil composition comprising:

mixing 40 to 99.7% by weight of a diglyceride comprising 15 to 89.5% by weight of $\omega 3$ type unsaturated acyl groups having at least 20 carbon atoms and 10 to 84.5% by weight monenoic acyl groups with 0.1 to 59.8% by weight of a triglyceride and 0.1 to 10% by weight of a monoglyceride, wherein said oil composition comprises at most 5% by weight of free fatty acid.

2. The method according to claim 1, wherein said $\omega 3$ type unsaturated acyl group having at least 20 carbon atoms is selected from the group consisting of eicosapentaenoyl, docosahexaenoyl and a mixture thereof.

3. The method according to claim 1, wherein said monenoic acyl group is selected from the group consisting of hexadecamonoenoyl, octadecamonoenoyl, eicosamonoenoyl, docosamonoenoyl and a mixture thereof.

4. The method according to claim 1, wherein said triglyceride is present in an amount of 5 to 55% by weight.

5. The method according to claim 1, wherein said diglyceride is present in an amount of 50 to 95% by weight.

6. The method according to claim 1, wherein said diglyceride is present in an amount of 60 to 90% by weight.

7. The method according to claim 1, wherein said monoglyceride is present in an amount of 0.1 to 5% by weight.

8. The method according to claim 1, wherein said diglyceride further comprises $\omega 6$ type unsaturated acyl groups.

9. The method of claim 8, wherein said $\omega 6$ type unsaturated acyl groups are present in an amount of 0.5 to 75% by weight.

10. The method of claim 8, wherein said $\omega 6$ type unsaturated acyl groups are present in an amount of 0.5 to 50% by weight.

11. The method wherein claim 8, wherein said $\omega 6$ type unsaturated acyl groups are present in an amount of 1 to 25% by weight.

12. The method of claim 8, wherein said $\omega 6$ unsaturated acyl group is selected from the group consisting of linoleyl, γ-linolenyl, arachidonyl and a mixture thereof.

13. The method according to claim 1, wherein said oil composition further comprises 0.1 to 10% by weight of a glyceride polymer.

14. The method according to claim 1, wherein the content of $\omega 6$ type unsaturated acyl groups in acyl groups constituting the diglyceride is 0.5 to 75% by weight.

* * * * *